US012558511B2

(12) United States Patent
 Hu

(10) Patent No.: US 12,558,511 B2
(45) Date of Patent: Feb. 24, 2026

(54) PORTABLE OXYGEN CONCENTRATOR

(71) Applicant: Nanjing Yinuoji Medical Technology Co., Ltd., Nanjing (CN)

(72) Inventor: Yahuan Hu, Nanjing (CN)

(73) Assignee: Intellifai Health, Inc., Wellesley, MA (US)

( * ) Notice: Subject to any disclaimer, the term of this patent is extended or adjusted under 35 U.S.C. 154(b) by 225 days.

(21) Appl. No.: 18/358,115

(22) Filed: Jul. 25, 2023

(65) Prior Publication Data

US 2023/0414895 A1     Dec. 28, 2023

Related U.S. Application Data

(63) Continuation of application No. PCT/CN2021/073975, filed on Jan. 27, 2021.

(51) Int. Cl.
 *A61M 16/10* (2006.01)

(52) U.S. Cl.
 CPC ....... *A61M 16/101* (2014.02); *A61M 2207/10* (2013.01)

(58) Field of Classification Search
 CPC ............... A61M 16/101; B01D 53/047; B01D 53/0473; B01D 53/053
 See application file for complete search history.

(56) References Cited

U.S. PATENT DOCUMENTS 4,584,001 A * 4/1986 Dechene ............ B01D 53/0446
                                                    96/114
7,431,753 B2 * 10/2008 Yoshida .................. C01B 13/02
                                                    128/204.22

2005/0103341 A1 * 5/2005 Deane ................. A61M 16/101
                                                    128/204.26
2006/0117957 A1 * 6/2006 McCombs ........... B01D 53/047
                                                    96/121
2006/0230931 A1 * 10/2006 Bliss .................... C01B 13/0259
                                                    95/130
2007/0137487 A1 * 6/2007 Whitley ............. B01D 53/0415
                                                    96/121

(Continued)

FOREIGN PATENT DOCUMENTS

CN        109019519 A    12/2018
CN        208791184 U     4/2019

(Continued)

*Primary Examiner* — Kathryn E Ditmer

(57)          ABSTRACT

A portable oxygen concentrator, including: a battery box, a base assembly, a molecular sieve mechanism, a compressor mechanism, an oxygen storage mechanism, an outer cover, and an operation panel. The compressor mechanism includes a compressor main body and a compressor shell. A side wall of the compressor shell is provided with an opening, where a circuit board is fixed. The compressor main body includes a compressor and a vibration damping assembly arranged at the bottom of the compressor. A first valve assembly is embedded between the compressor main body and the vibration damping assembly, and is connected with the molecular sieve mechanism and an air outlet of the compressor main body. A second valve assembly is embedded between the oxygen storage mechanism and the molecular sieve mechanism, and is connected with an inlet of the molecular sieve mechanism and the oxygen storage mechanism.

7 Claims, 9 Drawing Sheets

(56)  References Cited

U.S. PATENT DOCUMENTS

| | | | |
|---|---|---|---|
| 2008/0156193 A1 | 7/2008 | Wang | |
| 2011/0315140 A1* | 12/2011 | Shuman | A61M 16/101 |
| | | | 128/205.24 |
| 2012/0055480 A1* | 3/2012 | Wilkinson | A61M 16/10 |
| | | | 128/205.11 |
| 2012/0167888 A1* | 7/2012 | Taylor | A61M 16/10 |
| | | | 128/205.12 |
| 2013/0299005 A1* | 11/2013 | Enomoto | A61M 16/0816 |
| | | | 137/78.1 |
| 2014/0190348 A1* | 7/2014 | Richey | B01D 53/053 |
| | | | 96/116 |
| 2014/0345609 A1* | 11/2014 | Whitcher | C01B 13/0259 |
| | | | 128/202.26 |
| 2015/0182720 A1* | 7/2015 | Taylor | B01D 53/0438 |
| | | | 128/205.12 |
| 2015/0238721 A1* | 8/2015 | Rumph | B01D 53/0446 |
| | | | 128/202.26 |
| 2016/0022950 A1* | 1/2016 | Taylor | A61M 16/101 |
| | | | 96/111 |
| 2020/0309303 A1* | 10/2020 | Taylor | B01D 53/0415 |
| 2020/0361770 A1* | 11/2020 | Lee | B01D 53/0476 |
| 2020/0376226 A1* | 12/2020 | Galbraith | G16H 50/30 |

FOREIGN PATENT DOCUMENTS

| | | | |
|---|---|---|---|
| CN | 110104614 A | | 8/2019 |
| CN | 110980653 A | * | 4/2020 |
| CN | 210393710 U | | 4/2020 |
| CN | 111606306 A | | 9/2020 |
| EP | 0978477 A1 | * | 2/2000 |

* cited by examiner

PORTABLE OXYGEN CONCENTRATOR

CROSS-REFERENCE TO RELATED APPLICATIONS

This application is a continuation of International Patent Application No. PCT/CN2021/073975, filed on Jan. 27, 2021. The content of the aforementioned application, including any intervening amendments thereto, is incorporated herein by reference in its entirety.

TECHNICAL FIELD

The present disclosure relates to oxygen concentrators, and more particularly to a portable oxygen concentrator.

BACKGROUND

30% is considered as the most suitable oxygen concentration for human body, which is called "oxygen-enriched air" and "life-giving oxygen" in medical field. In an oxygen-enriched environment, the physical skills, brain intelligence and blood oxygen concentration of human body can reach the best state. The oxygen consumption of human brain accounts for 20% of the whole body, and the brain is particularly sensitive to hypoxia. Insufficient oxygen to the brain will cause various fatigue syndromes such as exhaustion, dizziness, insomnia, memory deterioration and anorexia, which will affect human intelligence and work efficiency. And timely oxygen supplementation can obviously improve the above symptoms.

At present, in the domestic and overseas, oxygen is produced primarily by cryogenic process, membrane separation, and pressure swing adsorption (PSA) separation. Among them, in cryogenic process, the system has a long start-up time, complicated operation and maintenance, and is suitable for centralized oxygen supply occasions with a large amount of oxygen production, such as oxygen stations. Membrane separation method has the advantages of simple equipment, safe operation and good economy of oxygen enrichment in small scale, but with the disadvantages of damageable membrane materials, low concentration of oxygen production and high requirements for use. Pressure swing adsorption is a new type of air separation method developed in the 1960s, making air separation to produce oxygen based on the selective adsorption performance of molecular sieve adsorbent on oxygen and nitrogen in the air. Compared with the chemical oxygen production method, the pressure swing adsorption uses air as raw material, which has a wide range of sources, low cost and safe non-polluting, thus has a large oxygen production capacity. Compared with the cryogenic method, the pressure swing adsorption offers a simple equipment, convenient start and stop, and production of different equipment according to the size of oxygen demand.

The main principle of the PSA is that the equilibrium adsorption capacity of $N_2$ on adsorbent molecular sieve is higher than that of $O_2$, so $N_2$ and $O_2$ can be separated. Moreover, the adsorption capacity is positively correlated with the adsorption pressure. Under higher pressure, the capacity of adsorbed nitrogen is large, while under lower pressure, the capacity of adsorbed nitrogen is small. Therefore, the adsorbed nitrogen can be removed from the adsorbent by lowering pressure, so that the adsorbent can be regenerated and recycled. The current market requires a miniature and portable product, for which this application provides a portable oxygen concentrator.

SUMMARY

An object of this application is to provide a portable oxygen concentrator, which has a miniaturized structure and excellent portability, and thus exhibits strong market competitiveness.

Technical solutions of this application will be specifically described as follows:

A portable oxygen concentrator, comprising:
a battery box;
a base assembly;
a molecular sieve mechanism;
a compressor mechanism;
an oxygen storage mechanism;
an outer cover; and
an operation panel;
wherein the base assembly is arranged on the battery box; the molecular sieve mechanism and the compressor mechanism are arranged on the base assembly; the oxygen storage mechanism is provided on an upper side of the compressor mechanism; the outer cover is provided outside the oxygen storage mechanism, the molecular sieve mechanism and the compressor mechanism, and is configured to cover the oxygen storage mechanism, the molecular sieve mechanism and the compressor mechanism; and the operation panel is arranged on a surface of the outer cover;
the compressor mechanism comprises a compressor main body and a compressor shell provided on an outside of the compressor main body; an opening is provided on a side wall of the compressor shell, and a first circuit board is fixed on the opening; a top of the circuit board is connected with the operation panel through a wire; a bottom of the first circuit board is provided with a connecting pin; a surface of the battery box is provided with a second circuit board for power conversion, and the connecting pin is insertedly connected to the second-circuit board;
the compressor main body comprises a compressor and a vibration damping assembly arranged at a bottom of the compressor; two ends of the bottom of the compressor are provided with an air inlet; the air inlet of the compressor is fixedly provided with a connecting seat; and two ends of a top of the compressor are each provided with an air outlet;
a first valve assembly is insertedly provided between the compressor and the vibration damping assembly; the first valve assembly is connected with the air outlet of the compressor and the molecular sieve mechanism; a second valve assembly is insertedly provided between the oxygen storage mechanism and the molecular sieve mechanism; and the second valve assembly is connected with the molecular sieve mechanism and an air inlet of the oxygen storage mechanism;
the oxygen storage mechanism comprises an oxygen storage tank; an oxygen supply port is provided on a top of the oxygen storage tank; an oxygen supply nozzle is movably arranged on the oxygen supply port; a plurality of fixing rods are circumferentially arranged at an inner wall of the outer cover; a top of each of the plurality of fixing rods is connected to an inner top wall of the outer cover; a bottom of the molecular sieve mechanism and a bottom of the compressor mechanism are respectively provided with a base; and a bottom of each of the plurality of fixing rods is connected to the base; and two inner side walls of the outer cover are each provided with a hanging component; the hanging component comprises a base portion and a head portion; the base portion of the hanging component is sleevedly provided on a corresponding one of the plurality of fixing rods; and the head portion is configured to extend to outside through the outer cover.

In an embodiment, both sides of the first circuit board are each provided with a plurality of electronic devices; the plurality of electronic devices are categorized into first devices and second devices according to a preset size, wherein a size of the first devices is larger than a size of the second devices; and the first devices are arranged on an inner surface of the first circuit board, and the second devices are arranged on an outer surface of the first circuit board.

In an embodiment, the vibration damping assembly comprises:

a filter cover plate;

a cotton filter; and a vibration damping seat;

wherein the filter cover plate is arranged on the surface of the battery box; the cotton filter is laid on an upper surface of the filter cover plate; the vibration damping seat is arranged on an upper side of the cotton filter; the base assembly covers on an upper side of the vibration damping assembly; a via hole is provided on the upper side of the vibration damping assembly, and is configured to allow the vibration damping seat to pass there through; and the vibration damping seat is connected to the connecting seat through the via hole.

In an embodiment, the vibration damping seat comprises a cylinder; and a lug extending outward along a bottom of the cylinder; the cylinder and the lug are integrally formed; a top of the cylinder is movably and insertedly connected with the connecting seat; a plurality of limiting holes are arranged at a circumference of the lug; a plurality of limiting columns corresponding to the plurality of limiting holes are arranged on the base assembly along a circumference of via hole; the cylinder has a hollow structure; the base assembly is provided with an air inlet; and air enters the portable oxygen concentrator from the air inlet of the base assembly and passes through the cotton filter, the cylinder, and the connecting seat to reach the air inlet of the compressor.

In an embodiment, both ends of a bottom of the molecular sieve mechanism are respectively provided with a first vent and a second vent facing the first valve assembly; the first valve assembly comprises a first electromagnetic valve and a second electromagnetic valve arranged side by side at two sides of the bottom of the compressor; an inlet of the first electromagnetic valve is connected to the air outlet of the compressor main body and the first vent; two outlets of the first electromagnetic valve are connected to two outlets of the second electromagnetic valve from directly below the compressor main body, respectively; an air discharge port is provided between one of the two outlets of the first electromagnetic valve and one of the two outlets of the second electromagnetic valve connected thereto; and an inlet of the second electromagnetic valve is connected to the second vent.

In an embodiment, the second valve assembly comprises an upper valve cover, a valve seat and a lower valve cover; the upper valve cover comprises a first channel and a second channel arranged in parallel; the lower valve cover comprises a third channel and a fourth channel arranged in parallel; a first valve groove and a second valve groove are arranged at a middle of the valve seat; a third electromagnetic valve is arranged in the first valve groove, and a fourth electromagnetic valve is arranged in the second valve groove; the first valve groove is communicated with the first channel and the second channel; the second valve groove is communicated with the third channel and the fourth channel; the middle of the valve seat is also provided with a first duckbill valve and a second duckbill valve; an inlet end of the first duckbill valve is connected to the first channel, and an inlet end of the second duckbill valve is connected to the second channel; and the second duckbill valve and an outlet end of the second duckbill valve are connected to the second valve groove.

In an embodiment, the oxygen storage mechanism comprises a detection component electrically connected with the first circuit board; the detection component comprises a micro-pressure sensor, a pressure sensor and an ultrasonic oxygen concentration sensor; the ultrasonic oxygen concentration sensor comprises an ultrasonic emitting end and an ultrasonic receiving end; the oxygen storage tank comprises a tank body and a cover body; an oxygen storage chamber is formed between the tank body and the cover body; a concentration detection chamber and an oxygen supply chamber are arranged in the oxygen storage chamber; the concentration detection chamber is communicated with the oxygen supply chamber; a top of the concentration detection chamber is provided with two through holes; the two through holes are respectively configured to accommodate the ultrasonic emitting end and the ultrasonic receiving end; a top of the oxygen supply chamber is connected to the oxygen supply nozzle; a side of the cover body is provided with a first pipeline, a second pipeline, a third pipeline and a fourth pipeline; an input end of the first pipeline and an input end of the second pipeline are respectively connected to an output end of the molecular sieve mechanism; an output end of the first pipeline is connected to the oxygen storage chamber; an output end of the second pipeline is connected to the concentration detection chamber; a first end of the third pipeline is connected to the concentration detection chamber, and a second end of the third pipeline is connected to the micro-pressure sensor; and a first end of the fourth pipeline is connected to the oxygen storage chamber, and a second end of the fourth pipeline is connected to the pressure sensor.

In an embodiment, both sides of a bottom of the outer cover are each provided with a plurality of air vents distributed in an array; an adapter plate is arranged on an upper side of the battery box, and a charging interface is arranged on the adapter plate; the charging interface is arranged inside one of the plurality of air vents; and the both sides of the outer cover are each provided with a ventilation window.

The present disclosure has the following beneficial effects.

Regarding the portable oxygen concentrator designed herein, a side wall of the compressor cover is directly replaced with a circuit board, such that the space occupation is reduced, thereby improving the utilization of an inner space of the oxygen concentrator.

A vibration-damping assembly is provided at the bottom of the compressor main body to absorb the vibration generated by the compressor main body, thereby reducing the working noise.

The internal structure of the portable oxygen concentrator is reinforced by a plurality of fixing rods and hanging components, allowing for good strength and effectively protecting the molecular sieve mechanism and the compressor mechanism during the carrying process.

Simultaneously, this disclosure has simple structure, convenient assembly, compact overall structure design, and high space utilization, allowing for improved portability and enhanced market competitiveness.

DESCRIPTION OF THE DRAWINGS

The accompanying drawings are provided to facilitate the understanding of technical solutions of the present disclosure, and constitute a part of the specification.

The drawings are intended to explain the present disclosure together with the embodiments, and do not constitute limitations to the present disclosure.

In the drawings.

1. battery box;
2. base assembly;
3. molecular sieve mechanism; 31. first air vent;
4. compressor mechanism; 41. compressor main body; 411. compressor; 412. connecting seat; 413. vibration damping assembly; 414. filter cover plate; 415. cotton filter; 416. vibration damping seat; 417. base air inlet; 418. air discharge port; 42. compressor cover; 43. opening; 44. circuit board; 45. connecting pin;
5. oxygen storage mechanism; 51. oxygen storage tank; 511. tank body; 512. cover body; 513. concentration detection chamber; 514. oxygen supply chamber; 515. through hole; 516. first pipeline; 517. second pipeline; 518. third pipeline; 519. fourth pipeline; 52. oxygen supply port; 53. detection component; 531. micropressure sensor; 532. pressure sensor; 533. ultrasonic oxygen concentration sensor;
6. outer cover; 61. fixing rod; 62. base; 63. hanging component;
7. first valve assembly; 71. first electromagnetic valve; 711. first inlet; 72. second electromagnetic valve; 721. second inlet; 722. first outlet; and 723. second outlet;
8. second valve assembly; 81. upper valve cover; 811. first channel; 812. second channel; 82. valve seat; 821. first duckbill valve; 822. second duckbill valve; 83. lower valve cover; 831. third channel; 832. fourth channel; 84. first valve groove; 85. second valve groove; 86. third electromagnetic valve; and 87. fourth electromagnetic valve.

DETAILED DESCRIPTION OF EMBODIMENTS

Figure 1:
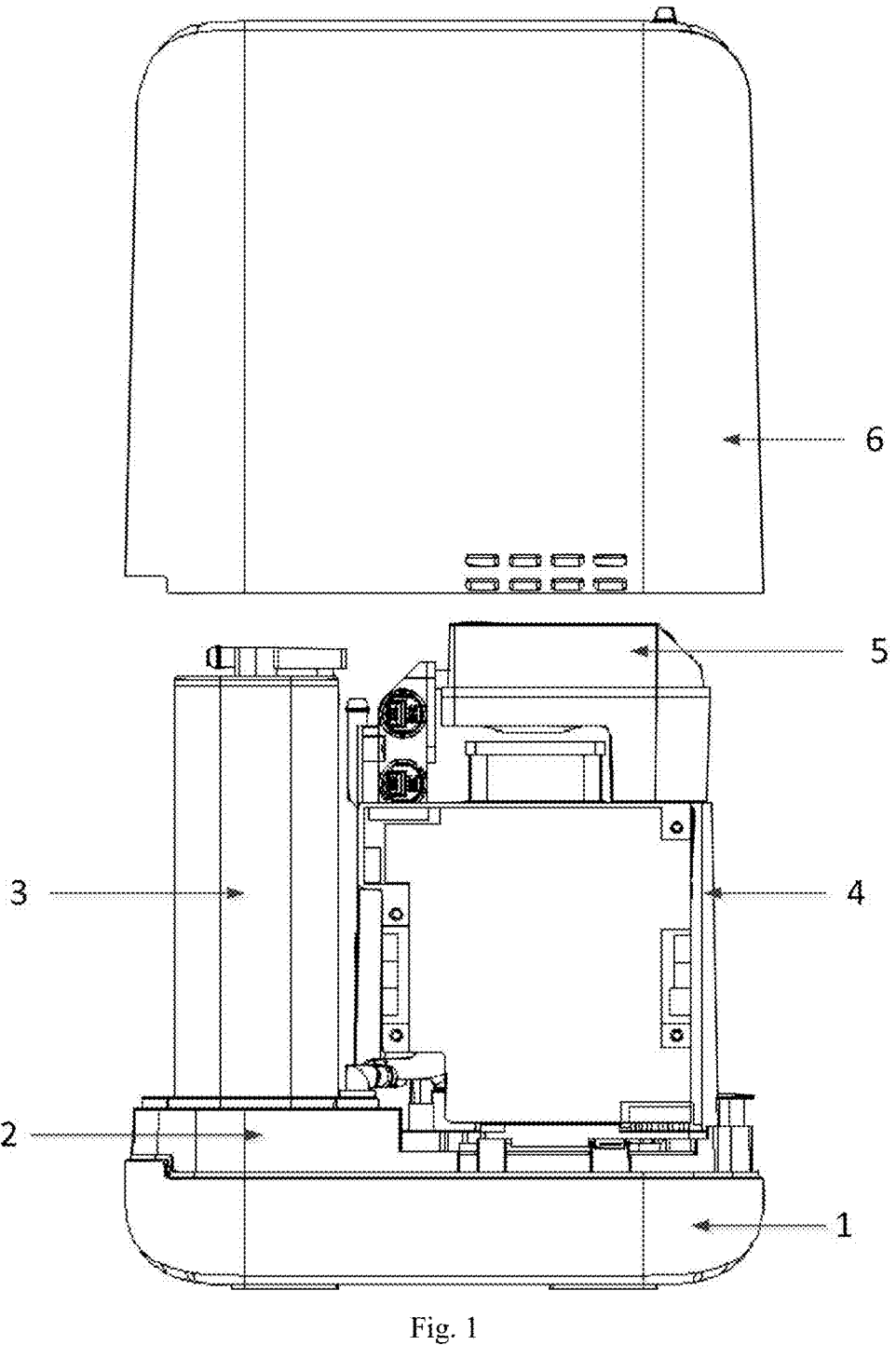
FIG. 1 is a schematic diagram of a portable oxygen concentrator according to an embodiment of the present disclosure.

As shown in FIG. 1, the portable oxygen concentrator includes:

a battery box 1;
a base assembly 2;
a molecular sieve mechanism 3;
a compressor mechanism 4;
an oxygen storage mechanism 5;
an outer cover 6; and
an operational panel.

The base assembly 2 is arranged on the battery box 1. The molecular sieve mechanism 3 and the compressor mechanism 4 are arranged on the base assembly 2. The oxygen storage mechanism 5 is provided on an upper side of the compressor mechanism 4. The outer cover 6 is provided outside the oxygen storage mechanism 5, and is configured to cover the oxygen storage mechanism 5, the molecular sieve mechanism 3 and the compressor mechanism 4. And the operational panel is arranged on a surface of the outer cover 6.

Figure 2:
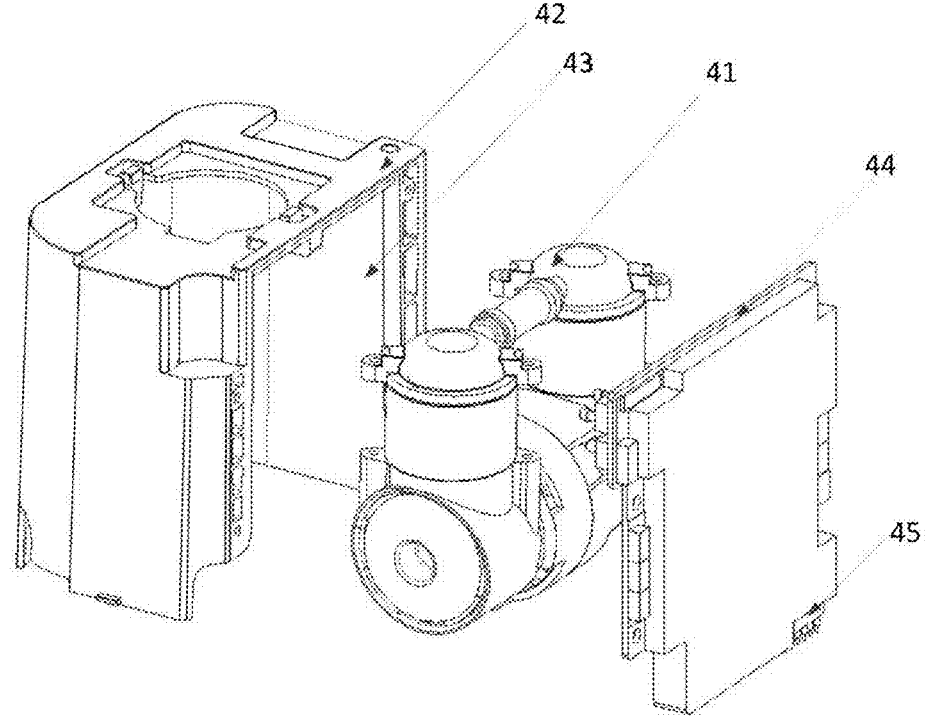
FIG. 2 is a schematic diagram of a circuit board mounting structure according to an embodiment of the present disclosure.

As shown in FIG. 2, the compressor mechanism 4 includes a compressor main body 41 and a compressor shell 42 provided on an outside of the compressor main body 41. An opening 43 is provided on a side wall of the compressor shell 42, and a first circuit board 44 is fixed on the opening 43. The first circuit board 44 is connected to the compressor shell 42 by a fastener configured to conveniently assemble and disassemble. A top of the first circuit board 44 is connected with the operation panel by a wire configured to realize communication interaction with the operator panel. A bottom of the first circuit board 44 is provided with a connecting pin 45. A surface of the battery box 1 is provided with a power conversion circuit board. The connecting pin is plugged into the power conversion circuit board configured to supply electricity to the first circuit board 44. In an embodiment, a plurality of electronic devices are arranged on both sides of the first circuit board 44. The plurality of electronic devices are categorized into first devices and second devices according to a preset size, wherein a size of the first devices is larger than a size of the second devices; and the first devices are arranged on an inner surface of the first circuit board 44 and the second devices are arranged on an outer surface of the first circuit board 44. The first devices can be placed on an inside of the first circuit board 44 and placed at a gap of the compressor main body 41. And the first devices can be a side wall of the compressor shell 42 without occupying the space individually, thereby improving the utilization of an inner space of the oxygen concentrator. Meanwhile, due to an uneven surface of the compressor main body 41, the space utilization can be further improved by placing large devices into the gap.

Figure 3:
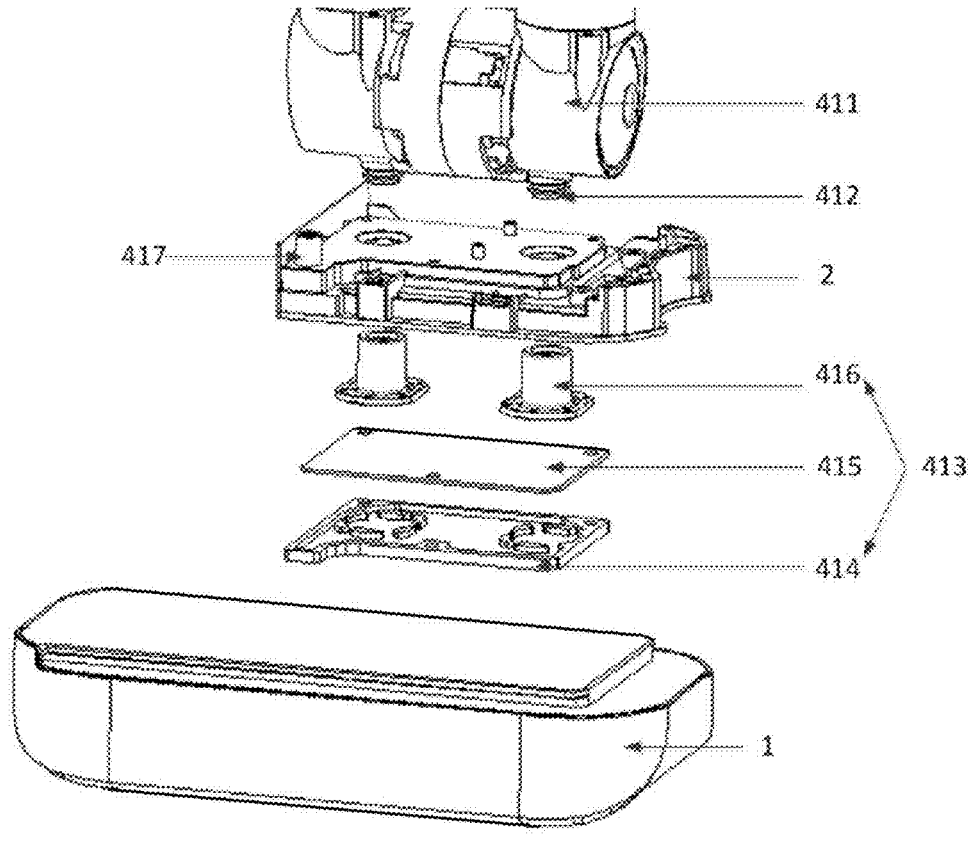
FIG. 3 is a schematic diagram of a compressor main body according to an embodiment of the present disclosure.

As shown in FIG. 3, the compressor main body 41 includes a compressor 411 and a vibration damping assembly 413 arranged at a bottom of the compressor main body 411. An inlet is provided at each bottom end of the compressor 411. The inlet of the compressor 411 is fixed with a connecting seat 412. An air outlet of the compressor is located at each top end, thereby connecting to the molecular sieve mechanism 3.

In an embodiment, the vibration damping assembly 413 includes a filter cover plate 414 arranged on a surface of the battery box 1, a cotton filter 415 laid on the upper surface of the filter cover plate 414 and a vibration damping seat 416 arranged on an upper side of the cotton filter 415. The base assembly 2 covers on an upper side of the vibration damping assembly 413. The base assembly 2 is provided with a via hole configured to allow the vibration damping seat 416 to pass through. The vibration damping seat 416 is connected to the connecting seat 412 through the via hole.

The vibration damping seat 416 includes a cylinder and a lug extending outward along a bottom of the cylinder. The cylinder and the lug are integrally formed. A top of the cylinder is movably and insertedly connected with the connecting seat 412. A plurality of limiting holes are arranged at a circumference of the lug. A plurality of limiting columns corresponding to the limiting holes are arranged on the base assembly along a circumference of via hole. The cylinder has a hollow structure. The base assembly 2 is provided with an air inlet 417. And air enters the portable oxygen concentrator from the air inlet 417 of the base assembly and passes through the cotton filter 415, the cylinder, and the connecting seat 412 to reach the air inlet of the compressor 411.

Figure 4:
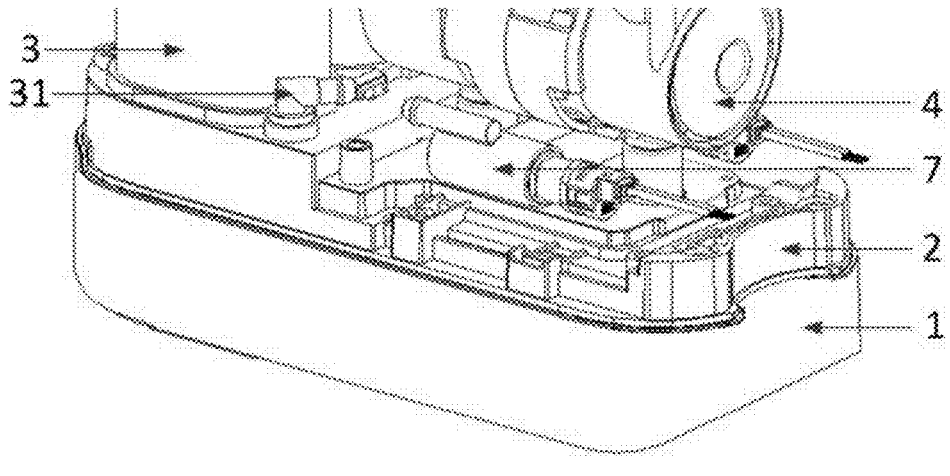
FIG. 4 schematically shows assembly of a first valve assembly according to an embodiment of the present disclosure.
Figure 5:
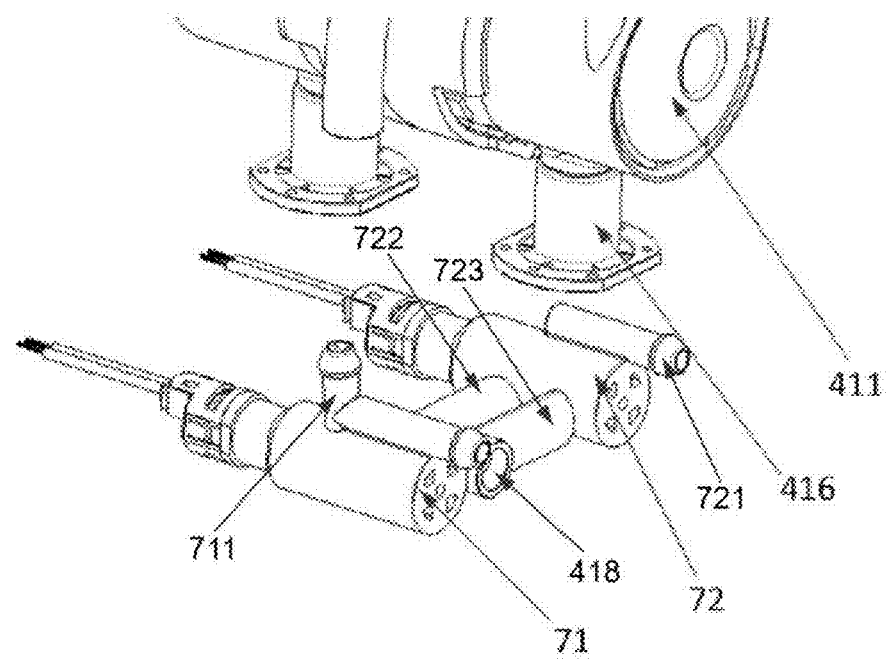
FIG. 5 schematically shows disassembly of the first valve assembly according to an embodiment of the present disclosure.

As shown in FIG. 4-5, a first valve assembly 7 is embedded between the compressor main body 41 and the vibration damping assembly 413. The first valve assembly 7 is connected with the air outlet of the compressor main body 41 and the molecular sieve mechanism 3. A first air vent 31 and a second air vent are provided at bottom ends of the molecular sieve mechanism 3 toward the first valve component 7 respectively. The first valve component 7 includes a first electromagnetic valve 71 and a second electromagnetic valve 72 provided side by side at the bottom sides of the compressor body 411. A first inlet 711 of the first electromagnetic valve 71 is connected to the air outlets of the compressor main body and the first air vent 31. Two outlets of the first electromagnetic valve 71 are connected to a first outlet 722 and a second outlet 723 of the second electromagnetic valve 72 from directly below the compressor main body 41. An air discharge port 418 is provided between one of the two outlets of the first electromagnetic valve 71 and one of the first outlet 722 and the second outlet 723 of the second electromagnetic valve 72, and a second inlet 721 of the second electromagnetic valve 72 is connected to the second air vent.

Figure 6:
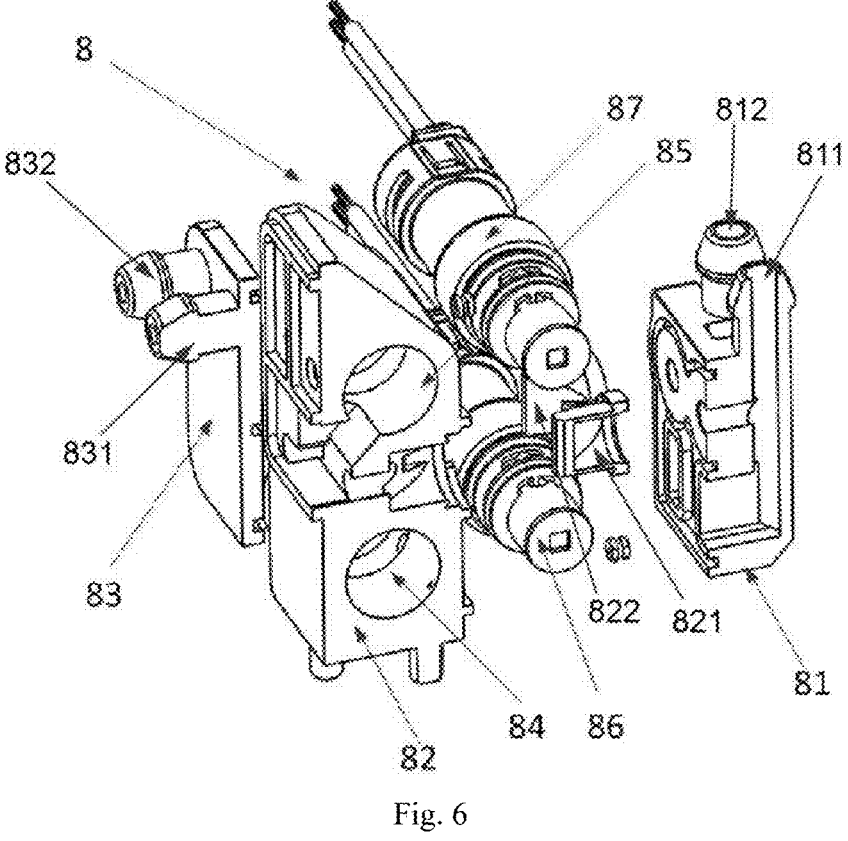
FIG. 6 schematically shows disassembly of the second valve assembly according to an embodiment of the present disclosure.

As shown in FIG. 6, a second valve assembly 8 is also embedded between the oxygen storage mechanism 5 and the molecular sieve mechanism 3. The second valve assembly 8 is connected with the molecular sieve mechanism 3 and the inlet of the oxygen storage mechanism 5. The second valve assembly 8 includes an upper valve cover 81, a valve seat 82 and a lower valve cover 83. The upper valve cover 81 includes a first channel 811 and a second channel 812 arranged in parallel. The lower valve cover 83 includes a third channel 831 and a fourth channel 832 arranged in parallel. A first valve groove 84 and a second valve groove 85 are arranged in a middle of the valve seat 82. A third electromagnetic valve 86 and a fourth magnetic valve 87 are arranged in the first valve groove 84 and the second valve groove 85 respectively. The first valve groove 84 is connected to the first channel 811 and the second channel 812 respectively. The second valve groove 85 is connected to the third channel 831 and the fourth channel 832 respectively. The middle of the valve seat 82 is also provided with a first duckbill valve 821 and a second duckbill valve 822. The first duckbill valve 821 and the second duckbill valve 822 are provided with an inlet and an outlet respectively. The inlet of the first duckbill valve 821 is connected to the first channel 811, and the inlet of the second duckbill valve 822 is connected to the second channel 812. The outlet of the first duckbill valve 821 and the outlet of the second duckbill valve 822 are connected to the second valve groove 85. The second valve assembly 8 is skillfully designed for the working principle of dual-cylinder integrated molecular sieve, so that the oxygen generated by the dual-cylinder integrated molecular sieve can be one-way guided. The duckbill valve and the inlet are configured to make the unidirectionality and sealability of the valve body more reliable. The third electromagnetic valve 86 and the fourth magnetic valve 87 are configured to make the supply of oxygen to the molecular sieve controllably return thereby accelerating the discharging of nitrogen in the molecular sieve, so as to improve the working efficiency of the molecular sieve.

Figure 7:
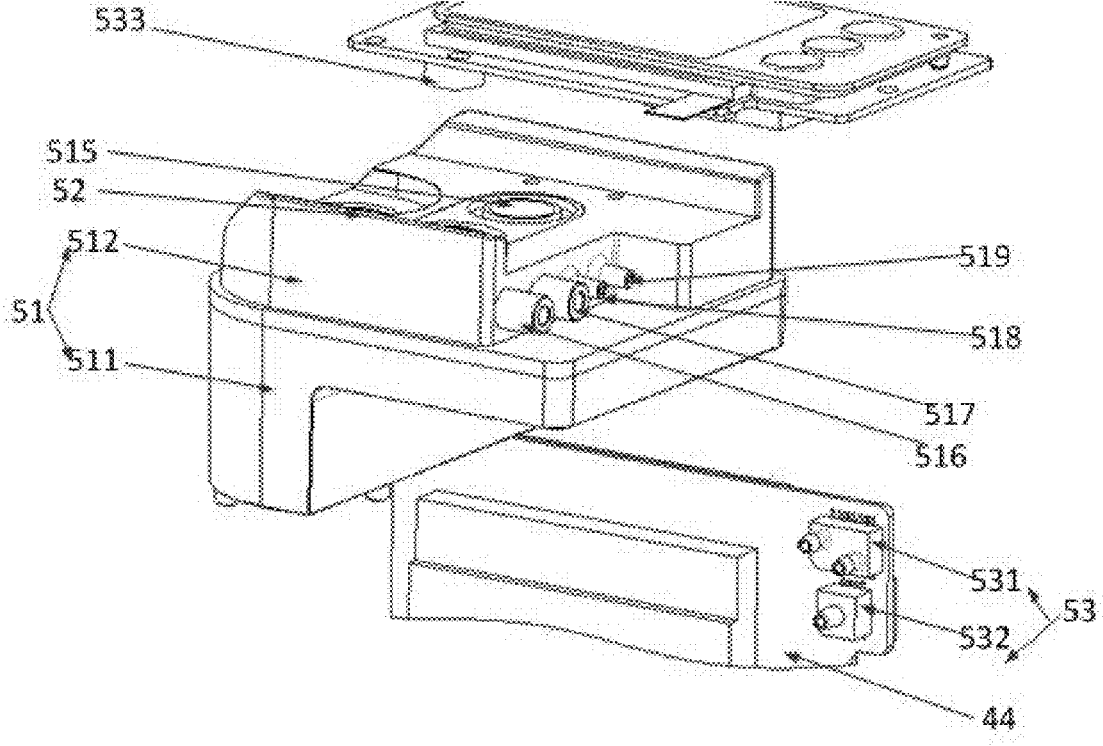
FIG. 7 is a schematic diagram of the oxygen storage mechanism according to an embodiment of the present disclosure.
Figure 8:
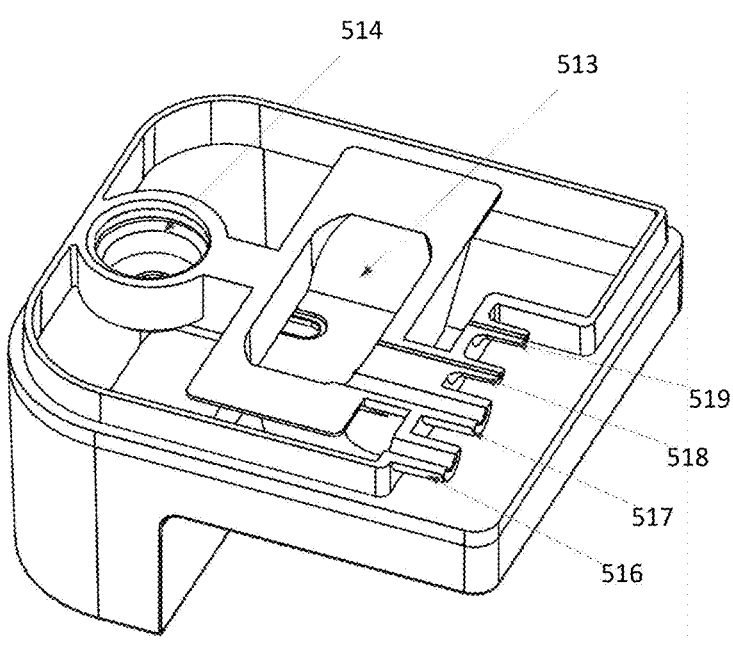
FIG. 8 schematically shows disassembly of the oxygen storage mechanism according to an embodiment of the present disclosure.

As shown in FIGS. 7-8, the oxygen storage mechanism 5 includes an oxygen storage tank 51. An oxygen supply port 52 is provided on a top of the oxygen storage tank 51. An oxygen supply nozzle is movably arranged on the oxygen supply port 52. The oxygen storage mechanism 5 includes a detection component 53 electrically connected with the first circuit board 44. The detection component 53 includes a micro-pressure sensor 531, a pressure sensor 532 and an ultrasonic oxygen concentration sensor 533. The ultrasonic oxygen concentration sensor 533 includes an ultrasonic emitting end and an ultrasonic receiving end. The oxygen storage tank 51 includes a tank body 511 and a cover body 512. An oxygen storage chamber is formed between the tank body 511 and the cover body 512, a concentration detection chamber 513 and an oxygen supply chamber 514 are arranged in the oxygen storage chamber. The concentration detection chamber 513 is connected with the oxygen supply chamber 514. A top of the concentration detection chamber 513 is provided with two through holes 515. The two through holes 515 are respectively configured to accommodate the ultrasonic emitting end and the ultrasonic receiving end. The top of the oxygen supply chamber 514 is connected to the oxygen supply nozzle. A side of the cover body 512 is provided with a first pipeline 516, a second pipeline 517, a third pipeline 518 and a fourth pipeline 519. An input end of the first pipeline 516 and an input end of the second pipeline 517 are respectively connected to an output end of the molecular sieve mechanism 3. An output end of the first pipeline 516 is connected to the oxygen storage chamber. An output end of the second pipeline 517 is connected to the concentration detection chamber 513. A first end of the third pipeline 518 is connected to the concentration detection chamber 513, and a second end of the third pipeline 518 is connected to the micro-pressure sensor 531. A first end of the fourth pipeline 519 is connected to the oxygen storage chamber, and a second end of the fourth pipeline 519 is connected to the pressure sensor 532. The oxygen storage chamber, the concentration detection chamber 513 and the oxygen supply chamber 514 are cleverly structured, do not interfere with each other, and the detection is accurate. The oxygen storage chamber is configured with the pressure sensor 532 to detect the oxygen pressure. The concentration detection chamber 513 is configured with the ultrasonic oxygen concentration sensor 533 to detect oxygen concentration and the micro-pressure sensor 531 to detect the user's breath. The oxygen supply chamber 514 is configured to provide oxygen to the user after the oxygen concentration is detected.

Figure 9:
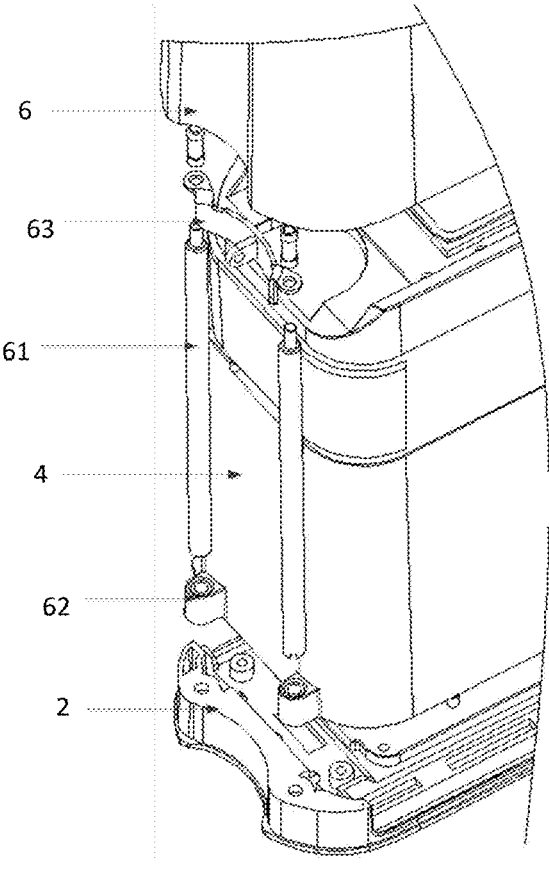
FIG. 9 schematically shows assembly of the outer cover according to an embodiment of the present disclosure.

As shown in FIG. 9, fixing rods 61 are respectively arranged around an inner wall of the outer cover 6. Atop of the fixing rods 61 are connected to a top inner wall of the outer cover 6. Bases 62 are respectively arranged at a bottom of the molecular sieve mechanism 3 and the compressor mechanism 4. A bottom of the fixing rods 61 are connected to the bases 62. Hanging components 63 are respectively arranged at both sides of the inner wall of the outer cover 6. The hanging components 63 include buckle seats and buckle heads; the buckle seats are respectively sleeved on the fixing rods 61. The buckles heads extend to the outside through the outer cover 6. Both sides of a bottom of the outer cover are each provided with a plurality of air vents distributed in an array. An adapter plate is arranged on an upper side of the battery box, and a charging interface is arranged on the adapter plate. The charging interface is arranged inside one of the plurality of air vents. And the both sides of the outer cover 6 are each provided with a ventilation window.

The above are only preferred embodiments of the present disclosure and not intended to limit the present disclosure. For those skilled in the art, various modifications and changes can be made to the foregoing embodiments of the present disclosure. It should be understood that any modification, equivalent substitution and improvement made within the spirit and principle of the present disclosure should be included within the scope of the present disclosure defined by the appended claims.

What is claimed is:

1. A portable oxygen concentrator, comprising:
   a battery box;
   a base assembly;
   a molecular sieve mechanism;
   a compressor mechanism;
   an oxygen storage mechanism;
   an outer cover; and
   an operation panel;
   wherein the base assembly is arranged on the battery box; the molecular sieve mechanism and the compressor mechanism are arranged on the base assembly; the oxygen storage mechanism is provided on an upper side of the compressor mechanism; the outer cover is provided outside the oxygen storage mechanism, the molecular sieve mechanism and the compressor mechanism, and is configured to cover the oxygen storage mechanism, the molecular sieve mechanism and the compressor mechanism; and the operation panel is arranged on a surface of the outer cover;
   the compressor mechanism comprises a compressor main body and a compressor shell provided outside the compressor main body; an opening is provided on a side wall of the compressor shell, and a first circuit board is fixed over the opening; a top of the first circuit board is connected with the operation panel through a wire; a bottom of the first circuit board is provided with a connecting pin; a surface of the battery box is provided with a second circuit board for power conversion, and the connecting pin is insertedly connected to the second circuit board;
   the compressor main body comprises a compressor and a vibration damping assembly arranged at a bottom of the compressor; two ends of the bottom of the compressor are each provided with an air inlet; each of the air inlets of the compressor is fixedly provided with a connecting seat; and two ends of a top of the compressor main body are each provided with an air outlet;
   a first valve assembly is insertedly provided between the compressor main body and the vibration damping assembly; the first valve assembly is connected with the air outlets of the compressor main body and the molecular sieve mechanism; a second valve assembly is insertedly provided between the oxygen storage mechanism and the molecular sieve mechanism; and the second valve assembly is connected with the molecular sieve mechanism and an air inlet of the oxygen storage mechanism;

the oxygen storage mechanism comprises an oxygen storage tank; an oxygen supply port is provided on a top of the oxygen storage tank; an oxygen supply nozzle is movably arranged on the oxygen supply port;

a plurality of fixing rods are circumferentially arranged at an inner wall of the outer cover; a top of each of the plurality of fixing rods is connected to an inner top wall of the outer cover; a bottom of the molecular sieve mechanism and a bottom of the compressor mechanism are respectively provided with a base of the base assembly; and a bottom of each of the plurality of fixing rods is connected to the base of the molecular sieve mechanism or the base of the compressor mechanism; and two inner side walls of the outer cover are each provided with a hanging component; each hanging component comprises a base portion and a head portion; the base portion of each hanging component is sleevedly provided on a corresponding one of the plurality of fixing rods; and each head portion is configured to extend to outside through the outer cover.

2. The portable oxygen concentrator of claim 1, wherein the vibration damping assembly comprises:
   a filter cover plate;
   a cotton filter; and
   a vibration damping seat;
   wherein the filter cover plate is arranged on the surface of the battery box; the cotton filter is laid on an upper surface of the filter cover plate; the vibration damping seat is arranged on an upper side of the cotton filter; the base assembly is configured to cover on an upper side of the vibration damping assembly; a via hole is provided in the base assembly, and is configured to allow the vibration damping seat to pass through; and the vibration damping seat is connected to one of the connecting seats through the via hole.

3. The portable oxygen concentrator of claim 2, wherein the vibration damping seat comprises:
   a cylinder; and
   a lug extending outward along a bottom of the cylinder;
   wherein the cylinder and the lug are integrally formed; a top of the cylinder is movably and insertedly connected with the one of the connecting seats; a plurality of limiting holes are arranged at a circumference of the lug; a plurality of limiting columns corresponding to the plurality of limiting holes are arranged on the base assembly along a circumference of the via hole; the cylinder has a hollow structure; the base assembly is provided with an air inlet; and air is configured to enter the portable oxygen concentrator from the air inlet of the base assembly and pass through the cotton filter, the cylinder, and the one of the connecting seats to reach a corresponding air inlet of the compressor.

4. The portable oxygen concentrator of claim 1, wherein two ends of the bottom of the molecular sieve mechanism are respectively provided with a first vent and a second vent facing the first valve assembly; the first valve assembly comprises a first electromagnetic valve and a second electromagnetic valve arranged side by side at two sides of the bottom of the compressor; an inlet of the first electromagnetic valve is connected to the air outlets of the compressor main body and the first vent; two outlets of the first electromagnetic valve are connected to a first outlet and a second outlet of the second electromagnetic valve from directly below the compressor main body, respectively; an air discharge port is provided between one of the two outlets of the first electromagnetic valve and one of the first and second outlets of the second electromagnetic valve connected thereto; and an inlet of the second electromagnetic valve is connected to the second vent.

5. The portable oxygen concentrator of claim 1, wherein the second valve assembly comprises an upper valve cover, a valve seat and a lower valve cover; the upper valve cover comprises a first channel and a second channel arranged in parallel; the lower valve cover comprises a third channel and a fourth channel arranged in parallel; a first valve groove and a second valve groove are arranged at a middle of the valve seat; a third electromagnetic valve is arranged in the first valve groove, and a fourth electromagnetic valve is arranged in the second valve groove; the first valve groove is communicated with the first channel and the second channel; the second valve groove is communicated with the third channel and the fourth channel; the middle of the valve seat is also provided with a first duckbill valve and a second duckbill valve; an inlet end of the first duckbill valve is connected to the first channel, and an inlet end of the second duckbill valve is connected to the second channel; and an outlet end of the first duckbill valve and an outlet end of the second duckbill valve are connected to the second valve groove.

6. The portable oxygen concentrator of claim 1, wherein the oxygen storage mechanism comprises a detection component electrically connected with the first circuit board; the detection component comprises a micro-pressure sensor, a pressure sensor and an ultrasonic oxygen concentration sensor; the ultrasonic oxygen concentration sensor comprises an ultrasonic emitting end and an ultrasonic receiving end; the oxygen storage tank comprises a tank body and a cover body; an oxygen storage chamber is formed between the tank body and the cover body; a concentration detection chamber and an oxygen supply chamber are arranged in the oxygen storage chamber; the concentration detection chamber is communicated with the oxygen supply chamber; a top of the concentration detection chamber is provided with two through holes; the two through holes are respectively configured to accommodate the ultrasonic emitting end and the ultrasonic receiving end; a top of the oxygen supply chamber is connected to the oxygen supply nozzle; a side of the cover body is provided with a first pipeline, a second pipeline, a third pipeline and a fourth pipeline; an input end of the first pipeline and an input end of the second pipeline are respectively connected to an output end of the molecular sieve mechanism; an output end of the first pipeline is connected to the oxygen storage chamber; an output end of the second pipeline is connected to the concentration detection chamber; a first end of the third pipeline is connected to the concentration detection chamber, and a second end of the third pipeline is connected to the micro-pressure sensor; and a first end of the fourth pipeline is connected to the oxygen storage chamber, and a second end of the fourth pipeline is connected to the pressure sensor.

7. The portable oxygen concentrator of claim 1, wherein opposite sides of a bottom of the outer cover are each provided with a plurality of air vents distributed in an array; an adapter plate is arranged on an upper side of the battery box, and a charging interface is arranged on the adapter plate; and the charging interface is arranged inside one of the plurality of air vents.

* * * * *